(12) United States Patent
Brauckman et al.

(10) Patent No.: US 6,749,553 B2
(45) Date of Patent: Jun. 15, 2004

(54) RADIATION DELIVERY DEVICES AND METHODS FOR THEIR MANUFACTURE

(75) Inventors: Richard A. Brauckman, Cumming, GA (US); Jack C. White, Alpharetta, GA (US); Glenn A. Dill, Fayetteville, GA (US); Michael R. Moody, Marietta, GA (US)

(73) Assignee: Theragenics Corporation, Buford, GA (US)

( * ) Notice: Subject to any disclaimer, the term of this patent is extended or adjusted under 35 U.S.C. 154(b) by 0 days.

(21) Appl. No.: 09/858,816

(22) Filed: May 16, 2001

(65) Prior Publication Data

US 2003/0204125 A1 Oct. 30, 2003

Related U.S. Application Data

(60) Provisional application No. 60/205,090, filed on May 18, 2000.

(51) Int. Cl.⁷ ............................. A61N 5/00; A61N 1/30; A61M 29/00
(52) U.S. Cl. ............................. 600/3; 604/19; 606/194
(58) Field of Search ............................. 600/1–8; 604/19, 604/53, 103, 104, 106, 107, 202, 93, 96; 606/194, 198, 1; 623/1.42, 1.21; 427/5; 376/158, 195, 201

(56) References Cited

U.S. PATENT DOCUMENTS

| 3,351,049 A | 11/1967 | Lawrence |
| 4,323,055 A | 4/1982 | Kubiatowicz |
| 4,509,506 A | 4/1985 | Windorski et al. |
| 4,697,575 A | 10/1987 | Horowitz |
| 4,706,652 A | 11/1987 | Horowitz |
| 4,754,745 A | 7/1988 | Horowitz |
| 4,754,754 A | 7/1988 | Garito et al. |
| 4,763,642 A | 8/1988 | Horowitz |
| 4,815,449 A | 3/1989 | Horowitz |
| 4,891,165 A | 1/1990 | Suthanthiran et al. |
| 4,946,435 A | 8/1990 | Suthanthiran et al. |
| 5,122,593 A | 6/1992 | Jennings et al. |
| 5,140,073 A | 8/1992 | Rolando et al. |
| 5,342,283 A | 8/1994 | Good |
| 5,405,309 A * | 4/1995 | Carden, Jr. ..................... 600/3 |
| 5,713,828 A | 2/1998 | Coniglione |
| 5,871,708 A | 2/1999 | Park et al. |
| 5,906,573 A | 5/1999 | Aretz |
| 5,938,583 A | 8/1999 | Grimm |
| 5,942,209 A | 8/1999 | Leavitt et al. |
| 6,010,446 A | 1/2000 | Grimm |
| 6,030,333 A | 2/2000 | Sioshansi et al. |
| 6,059,714 A | 5/2000 | Armini et al. |
| 6,132,359 A | 10/2000 | Bolenbaugh |
| 6,143,431 A | 11/2000 | Webster ..................... 428/205 |
| 6,149,574 A * | 11/2000 | Trauthen et al. ............... 600/3 |
| 6,264,600 B1 | 7/2001 | Grimm |
| 6,287,249 B1 * | 9/2001 | Tam et al. ..................... 600/3 |
| 6,458,069 B1 * | 10/2002 | Tam et al. ..................... 600/3 |
| 6,491,619 B1 * | 12/2002 | Trauthen et al. ............... 600/3 |

* cited by examiner

Primary Examiner—Mary Beth Jues
Assistant Examiner—Nikita R Veniaminov
(74) Attorney, Agent, or Firm—Knoble Yoshida & Dunleavy LLC

(57) ABSTRACT

Radiation delivery devices useful in brachytherapy which employ radioactive palladium-103 as the radiation source material are disclosed. Certain embodiments of the disclosed radiation delivery devices have the advantages that they can be fabricated with the desired specific activity, that the self-shielding effects of the devices are minimized, that the radioactive source material is bonded to a substrate in a manner which substantially prevents it from becoming detached, and that a variety of customizable radiation delivery devices can be made using the concepts of the invention. Also disclosed are processes for bonding radiation source material to various substrates using electroless plating, chemical vapor deposition and polymer matrices. These processes have the advantage that they can be applied to bond the radiation source material to a wide variety of substrates including different substrate materials and differently shaped substrates, thereby providing the ability to tailor the radiation delivery devices to the specific requirements of a particular brachytherapy treatment.

19 Claims, 7 Drawing Sheets

RADIATION DELIVERY DEVICES AND METHODS FOR THEIR MANUFACTURE

RELATED APPLICATION DATA

This application claims the benefit of U.S. provisional patent application No. 60/205,090, filed on May 18, 2000, pursuant to 35 U.S.C. §119(e).

FIELD OF THE INVENTION

The present invention relates to localized radiation therapy and devices therefore. More particularly, the present invention is directed to radiation delivery devices using palladium-103, and to their methods of manufacture.

BACKGROUND OF THE INVENTION

Radioactive materials have long been used in the medical treatment of diseased tissues. Such radioactive materials may be implanted into a patient at the site of the diseased tissue or may be locally applied externally through the skin. In either case, it is desirable to have the radioactive material in a form which will permit it to be used to irradiate the diseased tissue while minimizing damage to nearby healthy tissue. Therefore, it is desirable to have a radiation delivery device which will uniformly irradiate a diseased area with a controlled dosage of radiation while minimizing the exposure of surrounding healthy tissue to the radiation.

Interstitial implantation of radiation delivery devices for localized tumor treatment has long been recognized. The advantages of interstitial implants reside in their ability to concentrate the radiation in a localized area thereby minimizing radiation exposure to nearby healthy tissue. Commonly used implantable radioactive materials include iridium-192, iodine-125, gold-198 and radon-222. However, each radiation source type has limitations. For instance, most of these isotopes emit high energy gamma rays and the energy of their X-ray radiation is relatively low. Also, some of these isotopes have relatively long half-lives which make them less desirable for brachytherapy treatments.

Several types of radioactive implants are known from U.S. Pat. No. 5,342,283 (Good). This patent discloses radioactive implants such as microspheres, wires and ribbons coating with radioactive metals by, for example, sputtering. The radioactive implants disclosed in this patent are solid, seamless elements which may be individually implanted or combined in intercavity applicators with fabrics and in ribbons. A variety of different radioisotopes are disclosed.

U.S. Pat. No. 4,323,055 (Kubiatowicz) discloses a radioactive iodine seed wherein the carrier for the radioisotope is a rod-like member which is detectable by x-rays and occupies a substantial portion of the space within the seed. The radioactive iodine is distributed on the carrier body using an ion exchange process by first halogenating the carrier body and then conducting an ion exchange reaction with the radioactive material. Alternatively, the radioactive iodine can be electroplated onto the carrier body. The carrier body is placed within a biocompatible container such as a titanium capsule for use.

U.S. Pat. No. 5,713,828 (Coniglione) discloses a brachytherapy device formed from a hollow tube-shaped seed substrate which allows association of the device with suture material to prevent migration of the device in the body. The radioactive material is distributed on the exterior surface of the tubular device to provide a relatively uniform radiation field around the brachytherapy seed source. A tubular, biocompatible outer casing is placed around the inner, radioactive tube to seal the radioactive material within the device. A variety of radioactive materials are disclosed for use with the device.

In addition to the above mentioned radioactive materials, it is also known to use palladium-103 in radiation therapy. Generally, Pd-103 does not suffer from the high energy gamma radiation problems associated with the previously mentioned isotopes. Consequently, irradiation treatments employing Pd-103 radiation can be more localized than with other radioactive isotopes thereby reducing the potential for harm to nearby healthy tissue.

U.S. Pat. No. 4,702,228 describes therapeutic seeds containing Pd-103 prepared by increasing the Pd-102 or content found in palladium metal, i.e., by enriching palladium metal in Pd-102 or content and then by exposing it to a neutron flux in a nuclear reactor so as to convert a small fraction of the Pd-102 into Pd-103. Alternatively, Pd-104 enriched palladium can be employed in which case the Pd-104 will be exposed to proton bombardment to produce radioactive Pd-103.

Generally, palladium-103 is produced in a nuclear reactor by bombarding a target containing Pd-102 with neutrons (Pd-102(n,$\gamma$) Pd-103). Since all of the Pd-102 nuclei are not converted and, since in addition, other naturally occurring isotopes of the element palladium are typically present in small amounts in the target, Pd-103 cannot be produced in a carrier free state. By carrier-free state it is meant Pd-103 containing substantially no other palladium isotopes. Since there are small amounts other isotopes of Pd present in the target, neutron activation products of these isotopes are produced as well. For example, the reaction Pd-108(n,$\gamma$)Pd-109 also occurs and therefore Pd-103 obtained from a reactor by neutron bombardment always contains a small amount of the radioisotope Pd-109. Since Pd-109 is the same element as Pd-103, no chemical means are known to effect their separation. The presence of other nuclides of Pd in the target also leads to the production of significant amounts of certain non-Pd radioisotopes, e.g. if radioactive Pd-111 is produced, it will decay to another radioactive isotope, Ag-111, further complicating the radiochemical purification of the Pd-103 matrix. In contrast, Pd-103 produced in a particle accelerator, such as a cyclotron, may be obtained in a carrier-free state, i.e. containing substantially no palladium isotopes other than Pd-103.

Another drawback of radiation delivery devices produced in a nuclear reactor from Pd-102 enriched palladium is that for practical reasons soon to be apparent, one is obliged to use reactor grade Pd-103 at the specific activity level generated in the reactor. This places significant limitations on the level of dosage that can be delivered by a device which employs reactor grade Pd-103. In contrast, cyclotron-produced carrier-free Pd-103 can be employed in a way that provides for its economical utilization while at the same time providing for a device having a predetermined therapeutic or apparent activity.

The specific activity of Pd-103 that can be produced in a nuclear reactor is determined by the level of enrichment of the Pd-102 target used, the neutron flux in the reactor and the length of exposure of the target to the neutron flux in the reactor. Generally, the highest enrichment of Pd-102 available (Oak Ridge National Laboratories (ORNL)) has an isotopic purity of 77.9% Pd-102 with the remaining 22.1% of the target being made up of the other isotopes of Pd. The highest neutron flux available in the world is found in the ORNL HFIR facility where the level is approximately 2.6E 15 neutrons/cm$^2$ sec. This reactor runs in 21 day cycles with approximately 10 days between cycles. Due to the generation of extraneous isotopes such as Ag-111, the maximum practical irradiation time is two cycles. These factors taken together indicate the maximum specific activity that can be derived from a nuclear reactor target is approximately 345 Ci/g. In contrast, the specific activity of carrier-free Pd-103 can be as high as 75,000 Ci/g.

As such, smaller amounts of carrier-free Pd-103 can be employed in radiation delivery devices as compared to reactor grade Pd-103 in order to achieve the same level of activity. Additionally, a greater degree of control over the specific activity of a particular device can be exercised when using carrier-free Pd-103 since the only potential error factors which enter into this process are the measurement of the specific activity of the carrier-free Pd-103 and the provision of the right amount for the desired level of specific activity in the device. Therefore, for these reasons it is often preferably to employ carrier-free Pd-103 in radiation delivery devices.

U.S. Pat. No. 3,351,049 to Lawrence et al. suggests the use of carrier-free palladium-103 in therapeutic seeds. U.S. Pat. No. 5,405,309 to Carden, Jr. also discloses the use of carrier-free Pd-103 in therapeutic seeds wherein carrier-free Pd-103 is mixed with a small amount of palladium metal, electroplated onto a pellet of electroconductive material, and encapsulated within a biocompatible container. By virtue of the electroplating and encapsulating procedures, a certain degree of self-shielding was observed which affected the efficacy and potency of the therapeutic seeds. However, such procedures were deemed necessary for proper containment of the radiation source material. Further, the therapeutic seeds disclosed in these patents are somewhat limited in use by their rigid physical dimensions.

In view of the above, there has remained a need in the art for versatile radiation delivery devices which exhibit reduced self-shielding properties while effectively containing the radiation source material.

SUMMARY OF THE INVENTION

It is an object of certain embodiments of the present invention to provide radiation delivery devices comprising a substrate and a radiation source material adhered to the outer surface of the substrate or incorporated into the substrate, wherein the radiation source material comprises carrier-free Pd-103. A variety of different types of substrates may be employed depending primarily upon the particular application for which the device will be employed.

It is a further object of certain embodiments of the present invention to provide methods for deposition of a radiation source material onto a substrate.

It is yet another object of certain embodiments of the present invention to provide a radiation delivery device, wherein the substrate design, and/or the radiation source material configuration is such that the device may provide a non-uniform, i.e. directional, radiation distribution.

It is another object of certain embodiments of the present invention to provide a radiation delivery device comprising a substrate and a radiation source material deposited onto, or incorporated into the substrate, wherein the substrate is shaped to fill a body cavity and the radiation source material comprises palladium-103.

It is a still further object of certain embodiments of the present invention to provide a method for filling a body cavity with such a radiation delivery device.

DESCRIPTION OF THE PREFERRED EMBODIMENTS

Figure 1A:
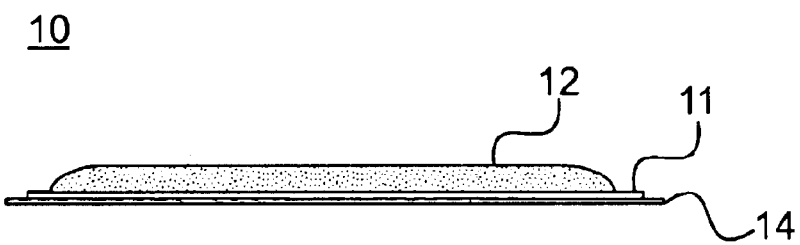
FIGS. 1A–1B illustrate a thin film radiation delivery device.

Generally stated, a radiation delivery device embodying features of the present invention comprises at least a radiation compatible substrate and a radiation source. The substrate and radiation source can either serve as a radiation delivery device, or the combination can be incorporated into a structure, which will serve as the radiation delivery device. The radiation source material is associated with the substrate in some way and, for example, can be incorporated into the substrate or applied onto the outer surface of the substrate.

Substrate

The substrate can be formed from a non-toxic metallic, non-metallic, polymeric, or ceramic material. The substrate can be in the form of a fiber, strand, ribbon, mesh, patch, film, suture, staple, clip, pin, microsphere, pellet, or the like. By pellet is meant substrates including, but not limited to, rods, cylinders and hollow tubes of different cross-sectional configurations. Further, the substrate can be rigid, flexible, deformable, solid, hollow, porous, or even sufficiently porous to allow for tissue growth therein.

In one embodiment, the substrate can be a thin film, fiber, ribbon, mesh, patch, suture, strand or the like formed from a biocompatible polymeric material. The polymeric material is preferably be selected from the group consisting of polyvinyl chloride, polysulfones, cellulose esters, nylon, Dacron™, polyesters, polyolefins, polyurethanes, polyamides, polyimides and modified versions of one or more of these materials, as well as any other polymeric materials known by a skilled person to be suitable for this purpose.

Radiation can cause degradation of certain polymeric materials, as is known in the art. Particularly preferred polymeric materials for forming the substrate are polymeric materials which are resistant to such degradation due to exposure to radiation, such as the radiation stabilized polypropylene materials disclosed in U.S. Pat. Nos. 5,122,593 and 5,140,073, the disclosures of which patents are hereby incorporated by reference to the extent that they relate to radiation stabilized polymeric materials suitable for use as substrates in the present invention.

Optionally, the polymeric materials forming the substrate can include one or more additives to enhance the adherence of the radiation source material to the substrate. Examples of such additives include absorbent materials such as activated carbon powder, activated charcoal, and ion exchange resins. Suitable ion exchange resins include sulfonated polystyrene resins, methylene-sulfonic phenolic resins, phosphoric polystyrene resins, polystyrene resins containing quaternary ammonium groups, pyridinium polystyrene resins, epoxy-polyamine resins containing tertiary and quaternary ammonium groups, acrylic resins, iminodiacetic polystyrene resins, and polystyrene resins containing polyamine groups, as well as other ion exchange resins known to persons skilled in the art.

In yet another embodiment, the substrate can be formed from a biodegradable polymeric material such as polyethylene glycol or polyethylene glycol-polyethylene oxide block copolymer. A particularly preferred substrate is made from a flexible or deformable material such as an elastomer, gel, foam or other suitable, flexible polymer material. Exemplary, but not limiting, polymeric materials include polyurethanes, silicones and elastomers, gels or foams of polyurethanes and silicones. Again, the key properties for use of these materials is that they must be suitable for implantation in the body and exhibit good radiation stability.

In an alternative embodiment, the substrate is a metallic material, which may be in the form of a pellet, or microsphere. The pellets or microspheres are preferably formed from a high atomic number metal or alloy such as aluminum, iridium, platinum, gold, tantalum, tungsten, lead and alloys of one or more of these or similar metals. Additionally, any lower atomic weight metal or alloy, which is satisfactorily visualized on radiographs may be used including molybdenum, indium, lithium, silver, copper, and stainless steel. Alternatively, when only magnetic resonance imaging of the delivery device is clinically desirable, the substrate can be a non-metallic pellet or microsphere formed from, for instance, carbon, diamond, or graphite or non-magnetic metals such as aluminum. The pellets or microspheres can be of any desired shape, but are preferably spherical or cylindrical. Of these substrates, graphite in the form of cylindrical pellets or microspheres is particularly preferred.

Radiation Source Material

The radiation source material preferably comprises carrier-free Pd-103, reactor grade Pd-103 or a mixture thereof. In addition, the radiation source material may optionally include a diluent as described below. The term "specific activity" as used herein and in the appended claims means the total activity of the Pd-103 per gram of the radiation source material.

Reactor grade Pd-103 may be prepared in any suitable conventional manner such as by activation of palladium metal or by fabrication in a nuclear reactor. One disadvantage of reactor grade Pd-103 is that it may contain trace amounts other undesirable radioactive palladium isotopes such as Pd-109 which emit potentially harmful types of radiation. Reactor grade Pd-103 can be fabricated to minimize such impurities. Nevertheless, in some applications, particularly those where irradiation will occur close to a vital internal organ, it may be desirable to avoid use of reactor grade Pd-103 for this reason. Moreover, the specific activity of reactor grade Pd-103 is relatively low as compared with other forms of radioactive palladium-103.

The term "carrier-free palladium-103" as used herein claims means palladium-103 which is fabricated in a particle accelerator such that it is essentially free from palladium isotopes other than palladium-103. Carrier-free Pd-103 is typically a highly pure material which contains essentially no undesirable radioactive isotopes of palladium. Moreover, carrier-free Pd-103 can be made having extremely high activities relative to reactor grade Pd-103 thereby providing greater flexibility in adjusting the specific activity of the radiation delivery device and permitting the use of smaller quantities of the expensive palladium material to achieve a desired level of radiation dose. In accordance with the present invention, carrier-free Pd-103 can preferably be prepared in a particle accelerator in accordance with the procedure given in Example 1 below.

In a preferred embodiment, the radiation source material further comprises a diluent. The diluent can be added to the radiation source material after it is eluted off the final purification anion exchange column. Alternatively, the diluent can be added during or prior to a purification process, if the diluent properties so allow. Suitable diluents for radioactive Pd-103 may include palladium metal, rhodium metal, one or more of the various substrate materials listed above, or any other suitable material which is compatible with the radiation released by the Pd-103. More preferred diluents are biocompatible materials. Preferred diluents for carrier-free palladium are rhodium and palladium metals, usually in the form of a soluble metal salt such as $PdCl_2$. Because palladium metal will have the same affinity for an anion exchange column as the Pd-103, it can be added as a diluent prior to a purification step employing an anion exchange column and can be co-purified along with the radioactive Pd-103.

Other preferred diluents are certain polymeric materials which can be employed as a diluent by, for example, homogeneously mixing the radiation source material with the polymer prior to its application to the substrate, or even by carrying out such mixing and using the mixture of polymeric material and radiation source material as the substrate itself.

Although the diluent may normally be considered an undesirable additive in a low energy emitting radiation source due to self-shielding effects, its addition in accordance with the present invention has been found to be advantageous in several respects which, in some applications, may make use of such a diluent desirable. Foremost, the added diluent can serve to promote strong adhesion of the radiation source material to the substrate, thereby forming a physiologically inert layer which will not allow the radioactive Pd-103 to be mobilized into the circulation of a patient being treated.

Secondly, the addition of diluent provides the ability to adjust the specific activity of the Pd-103 in the radiation source material. This adjustment can be employed to provide an accurately determined desired level of therapeutic or apparent activity, as well as to compensate for the self-shielding effects of the diluent. Thirdly, if purification of the carrier-free Pd-103 is necessary, the presence of the diluent can, in some instances, reduce the loss of Pd-103 occurring during the purification process.

The amount of diluent added, therefore, will vary depending principally upon the amount of carrier-free Pd-103 available. Preferably, from about 0.1 mg to about 100 mg of diluent per millicurie of radioactive source material area can be used. More preferably, from about 1 mg to about 50 mg of diluent per millicurie of radioactive source material is employed. Such amounts of diluent can ensure uniformity of the radioactive Pd-103 in the radiation delivery device and can promote adherence of the radiation source material to the substrate.

If design considerations, e.g., the desired mass or therapeutic activity of the delivery device, so allow, nuclear reactor produced Pd-103 can be added as a diluent to carrier-free Pd-103 and vice versa. Such addition may be employed, for example, to adjust the therapeutic activity of the radiation delivery device or to reduce the overall cost.

Radiation Source Material Incorporation Processes

As mentioned previously, the radiation source material can be applied to the outer surface of the substrate or be incorporated into the substrate. Particularly preferred methods for applying the radiation source material onto the surface of the substrate include electroless plating, electroplating, sputtering, ion implantation including ion exchange processes, physical vapor deposition or chemical vapor deposition ("CVD"). Other processes for associating a radioactive source material with a substrate known to persons skilled in the art may also be employed.

Electroless plating of Pd-103 onto a substrate has the advantage that it the process is applicable to a wide variety of substrates and is particularly useful for applying radioactive source material to non-conductive substrates. The process of the invention involves a first step of cleaning the substrate surface to which the plating will be applied. Conventional cleaning processes can be employed such as ultrasound, rinsing with solvents and/or water, and other known surface cleaning processes. Once cleaned, the surface of the substrate is pretreated with, for example, $SnCl_2$, a platinum salt or a palladium salt such as $PdCl_2$.

The pretreated substrate is then treated with, for example, a $PdCl_2$/HCl solution. The stannous ions cause the $Pd^{2+}$ ions from $PdCl_2$ to reduce to $Pd^0$ and to adhere to the substrate. These $Pd^0$ sites form a catalytic surface on the substrate to enhance the deposition of Pd-102enriched palladium, Pd-104 enriched palladium or radioactive Pd-103 onto the substrate in a subsequent plating step. Other, similar metals, such as platinum group metals, may also be used instead of palladium.

The Pd-102 or Pd-104 enriched palladium or radioactive Pd-103 can then be deposited on the activated substrate by submerging the substrate in a heated solution of Pd-102 or Pd-104 enriched palladium or radioactive Pd-103. Once the deposition reaction subsides, the substrate plated with Pd-102 or Pd-104 enriched palladium or radioactive Pd-103 is then dried and cooled. The electroless plating process has the additional advantages that there is very little loss of expensive palladium during the process and that a substantially uniform coating can be applied to a substrate in a relatively short time period. Also, the electroless plating process can be employed to apply a conductive coating onto a non-conductive substrate as a pretreatment of the substrate to prepare it for a subsequent electroplating step. Processes for electroplating palladium-103 onto various electroconductive substrates are known to persons skilled in the art from U.S. Pat. No. 5,405,309, the disclosure of which is incorporated by reference for the purpose of describing the details of a suitable electroplating process.

Alternatively, the radiation source material can be uniformly mixed with a diluent and then coated onto the outer surface of the substrate. Suitable diluents for this purpose include those described above as well as the substrate materials described above which may be used in polymer masterbatching processes, for example. Preferred diluents are adhesives and polymeric materials such as, for example, urethanes, acrylics, chloroprenes, polyvinylalcohols, polyvinylchlorides, nylons, or the like. It is preferred that the palladium be in solution when a diluent is use, for example, in the form of palladium chloride or palladium amine complex in solution, optionally in the diluent as the solvent.

In embodiments where the radiation source material is incorporated directly into the substrate, this can be accomplished, for example, using ion implantation or by physically mixing the radiation source material with the substrate material and then forming the substrate from the mixture. For instance, the radiation source material can be uniformly mixed with a polymer powder and be incorporated into the polymer matrix upon polymerization to form the substrate. Such a process is also applicable and particularly preferred when employing elastomer, foam or gel substrates. In a more preferred process, the radiation source material is mixed with a polymeric material and subsequently coated, plated or otherwise adhered to the outer surface of the substrate to form an outer, radioactive layer. This delivery device has the advantages that the radiation source material is firmly held in place in the polymer matrix, while at the same time the bulk of the radiation source material is located close to the surface of the substrate to thereby minimize self-shielding effects.

In certain preferred embodiments of the present invention, the radiation source material may be applied to the outer surface of a polymer pellets, microspheres, powders or other similar materials and then the solid polymers containing radioactive source material are physically mixed with a substrate material as described above. These embodiments are similar to polymer masterbatching techniques known to skilled persons for the purpose of incorporating various additives into polymeric materials.

The radiation source material can be supplied to above-described incorporation processes as a solid or in solution, as may be appropriate for the particular incorporation process. If supplied as a solid, the radiation source material can be carrier-free Pd-103 powder, or a mixture of carrier-free Pd-103 and a suitable solid diluent. Alternatively, the radiation source material may be supplied as solid reactor grade radioactive Pd-103 or as a solid form of Pd-102 or Pd-104 enriched palladium which may later be activated to radioactive Pd-103, in situ, after application of the Pd-102 or Pd-104 to the substrate of the radiation delivery device.

If supplied as a solution, the radiation source material can be, for example, a palladium amine complex obtained directly from a purification process. Alternatively, Pd-102 or Pd-104 enriched palladium or Pd-103 can be dissolved in an appropriate solvent to obtain a desired solution for a particular incorporation process. Suitable solvents for these materials are known in the art.

Delivery Devices

As discussed above, the substrate can itself serve as the radiation delivery device, or the substrate and radiation source can be incorporated into a structure, which serves as the radiation delivery device. In any event, the term, "therapeutic activity" or "apparent activity" as used herein and in the appended claims means the total activity of the Pd-103 as determined from measuring the radiation intensity just outside the radiation delivery thereby taking into account the self-shielding properties of Pd-103 and any other materials contained in the device which may shield the radioactivity. A particularly suitable method for measuring the activity of a device is the Air Kerma method certified by the U.S. National Institute of Standards.

In a preferred embodiment of the present invention, the device the radiation source material coated onto the outermost surface of a substrate or dispersed into the outermost layer of the substrate. The radiation delivery devices of the present invention can be implanted at one or more selected sites within a living body to emit localized radiation. The selected implantation site can be located near a target site to be treated. Alternatively, the delivery device can be implanted directly into a body cavity to be treated wherein the delivery device is shaped such that, when implanted, it substantially fills the body cavity to be treated. As is apparent to one of ordinary skill, such a body cavity can be naturally occurring within the body, artificially created as by surgery, or a combination thereof.

Figure 1B:
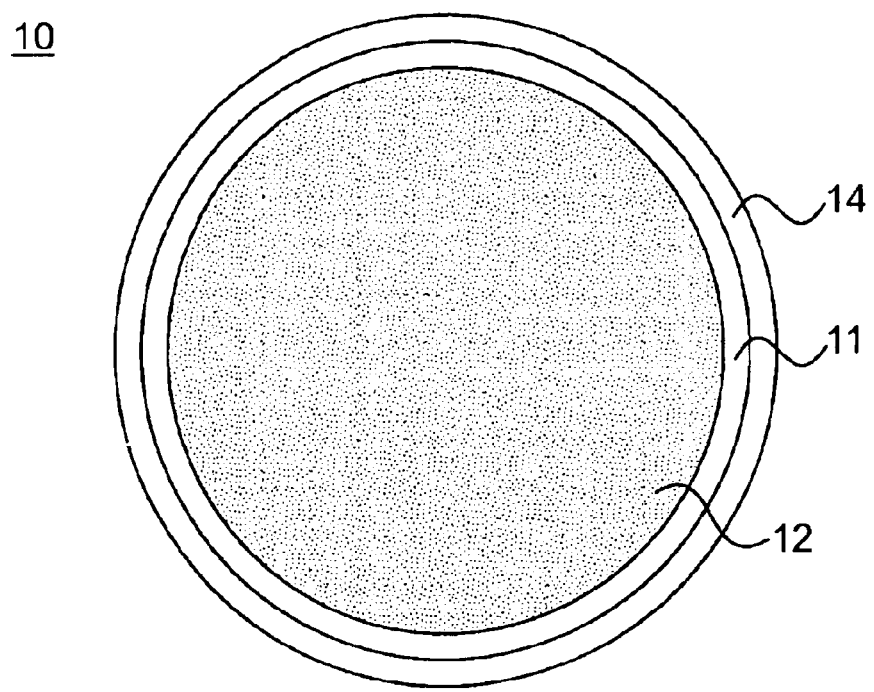

As shown in FIGS. 1A–1B, films provided with a radioactive material can serve as radiation delivery devices either directly or in the form of a patch. Such a radiation delivery device can, for example, be sutured in place or an adhesive can be applied to one surface of the device to adhere it in place. Other suitable means known to skilled persons for attaching films, patches or bandages to the body can also be employed to secure the film-based delivery device in place for treatment.

As shown in FIGS. 1A–1B, a film-based radiation delivery device 10 can be provided by securing a radiation source material 12 to a film substrate 11 by any of the processes described above for incorporation of the radiation source material into or onto substrate 11. In addition, radiation source material 12 can be adhered to film substrate 11 by mechanical attachment such as an adhesive layer 14 or any other suitable mechanical attachment known to suitable by skilled persons. The radioactive source material 12 may be coated on the surface of the film substrate 11 or may be incorporated directly into the film substrate 11. If the radioactive source material is directly incorporated into the film substrate 11, it is preferably located close to the outer surface of the film substrate 11.

The film-based radiation delivery device 10 is particularly suitable for treatment of areas having a flat surface or areas where the film substrate 11 can be attached to the body by, for example, sutures, adhesive material or other suitable attachment means or the film can be shaped to the contour of the body tissue in the treatment zone. In a preferred embodiment, the film substrate 11 is absorbable so that the film-based radiation delivery device 10 can be implanted and left in place permanently.

Figure 2:
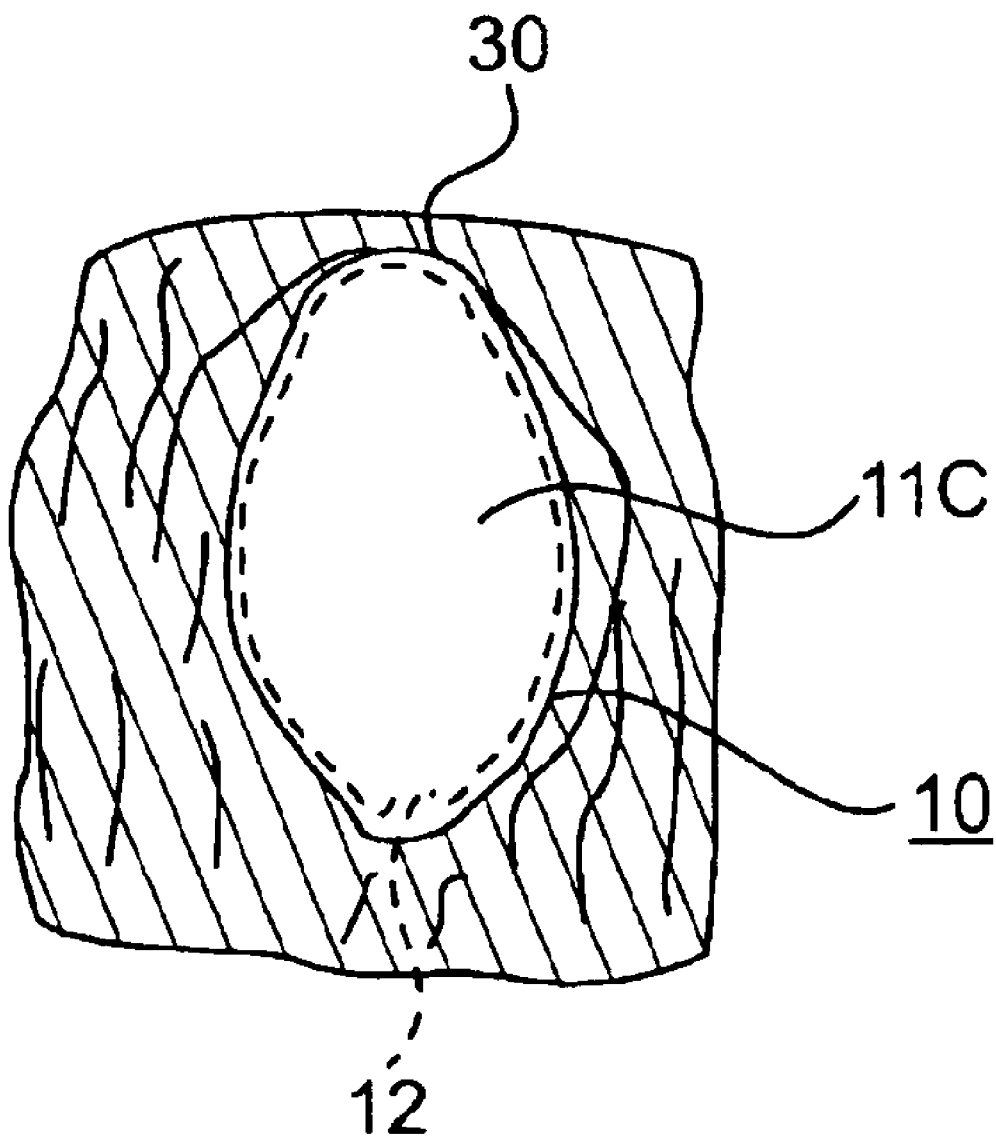
FIG. 2 shows a deformable radiation delivery device which may be implanted within a body cavity.

Referring now to FIG. 2, another aspect of the present invention provides a flexible or deformable delivery device 10. Such a flexible delivery device 10 can employ a substrate such as an elastomer, gel, foam or the like as the carrier for the radioactive source material. Such a flexible delivery device 10 is particularly suitable for use in customizable radioactive implants or delivery systems. For example, any biocompatible, radiation stable device having an internal cavity can be employed to deliver the flexible delivery device 10 of the present invention since the flexible material can be conformed to the shape and size of the cavity for each use. As a result, a hospital can have a supply of radioactive material on hand which can be employed in a variety of different types of delivery systems for different applications and indications.

The flexible or deformable delivery device 10 can also be used, for example, in a method for substantially filling a body cavity 30 with a radiation delivery device 10. Such a method involves the step of implanting a radiation delivery device 10 into a body cavity 30, wherein the radiation delivery device 10 is shaped such that, when implanted, it substantially fills the body cavity to locally emit radiation therein. The radiation delivery device 10 employed in this embodiment preferably comprises a deformable substrate 11c with a radiation source material 12 located on its outer surface or impregnated or absorbed in an outer layer of the deformable substrate 11c. The deformable substrate 11c enables the delivery device to conform to the contours of the body cavity 30. The flexible or deformable delivery device 10 may also be shaped to conform to a particular body structure depending upon the treatment application.

The flexible or deformable delivery device 10 may also be used in combination with one or more of the other embodiments of the invention described below. For example, a flexible hollow tube 21 can be filled with an elastomer, foam or gel containing radioactive material to provide a radiation delivery device. Other combinations of this embodiment with other embodiments of the invention are also possible, particularly if it is desirable to customize the radiation dose of a particular device on site for use.

Figure 3A:
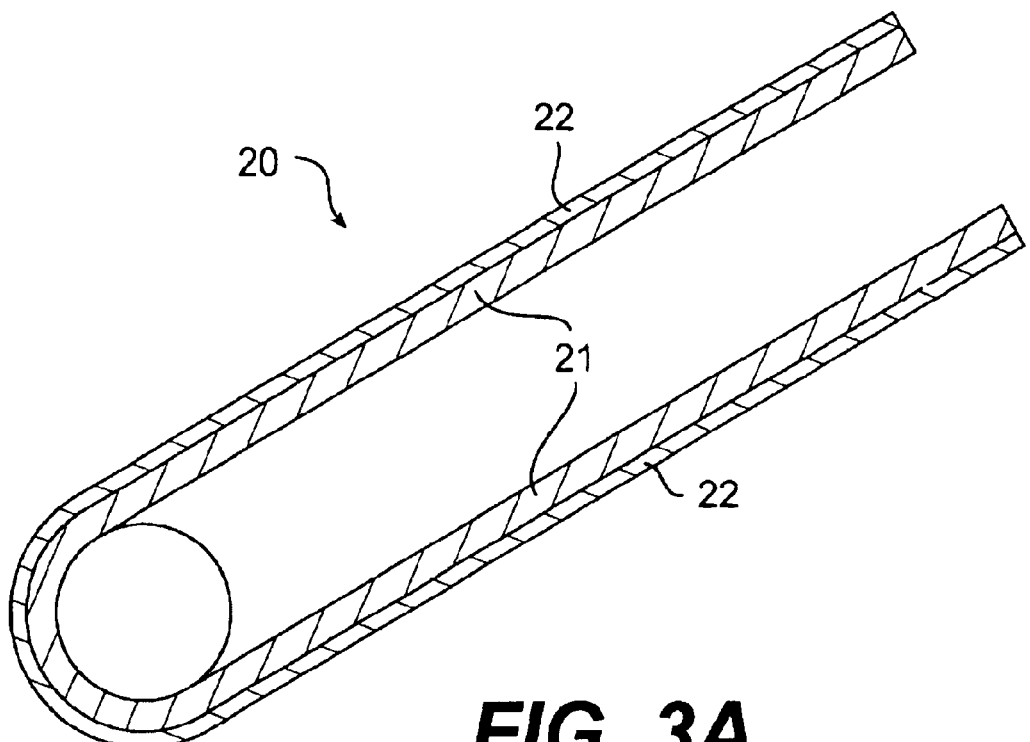
FIGS. 3A–3B show flexible hollow tube radiation delivery devices with a radioactive material on either an internal or external surface of the device.
Figure 3B:
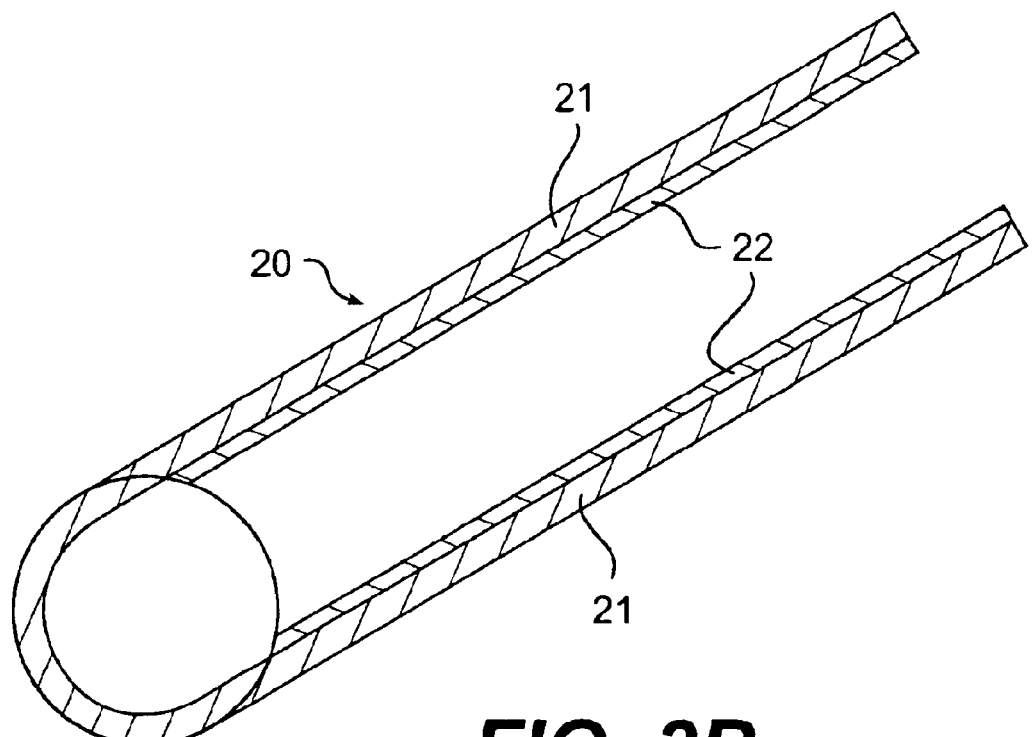

Referring to FIGS. 3A–3B, there is shown flexible hollow cylindrical tubular radiation delivery devices 20. The flexible tube 21 is formed from a deformable substrate such as the polymers mentioned above. In FIG. 3A is shown a flexible hollow tube 21 having a coating of radioactive material 22 on the outer surface thereof. In FIG. 3B is shown a flexible hollow tube 21 having a coating of radioactive material 22 on the inner surface of the flexible tube 21. The radioactive material may also form part of flexible tube 21 in which case it is preferably dispersed evenly throughout the material of flexible tube 21 or evenly over an area located adjacent to the outer surface of flexible tube 21.

This flexible tube 21 can be used in a variety of applications either alone or in combination with a housing or affixation device to house or affix the flexible tube 21 for the treatment process. In one embodiment, the flexible tube can be sutured in place by running sutures through the center of flexible tube 21. In another embodiment, flexible tube 21 can be attached to a catheter for delivery to a desired treatment zone. Preferably, flexible tube 21 is fabricated in lengths such that it can be cut to the desired length for a particularly treatment.

Figure 4:
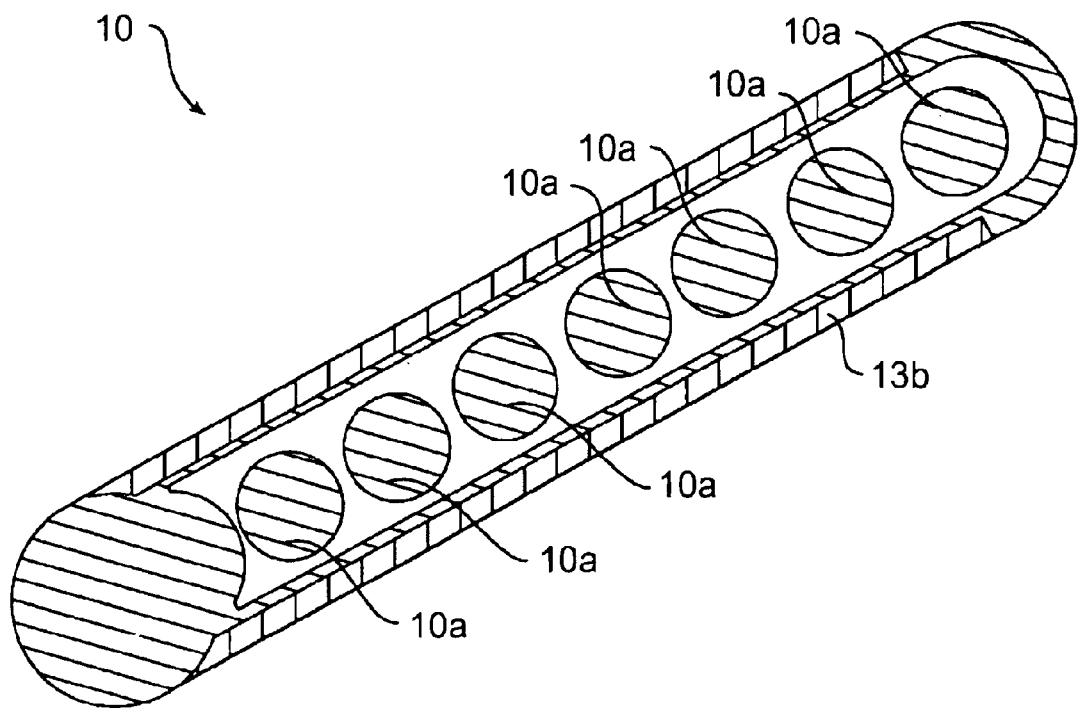
FIG. 4 shows a flexible hollow tube radiation delivery device which houses radioactive components.

FIG. 4 shows a flexible radiation delivery device 10 including a capsule 13b filled with microspheres 10a. The capsule 13b can be fabricated to any desired length or capsule 13b can be fabricated and then a section can be cut to the desired size for each specific application of the radiation delivery device. The number of microspheres 10a associated with the containment structure can vary depending on the desired therapeutic activity as well as the activity of each microsphere 10a. Alternatively, pellets may be employed instead of microspheres 10a. In this manner, customized delivery devices having a variety of shapes, sizes and therapeutic activities can be manufactured at low cost with little waste.

Figure 5:
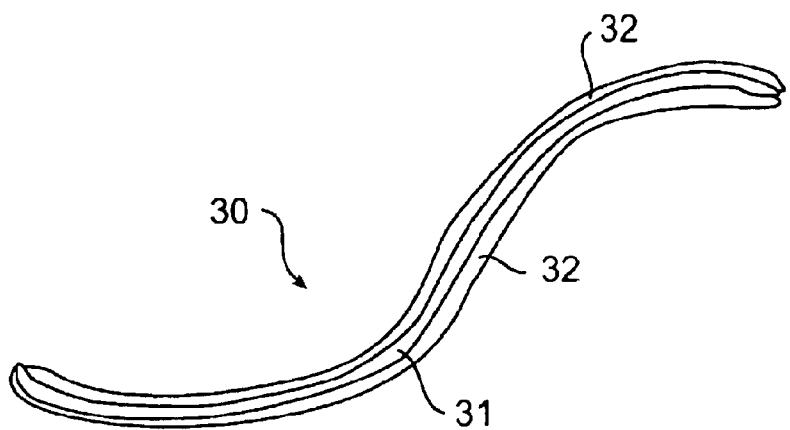
FIG. 5 shows a long flexible strand with a radioactive material on a surface of the strand.

FIG. 5 depicts a radiation delivery device 30 fabricated from a long flexible strand 31, which may be made from any of the various polymers mentioned above. Radioactive material 32 is preferably coated on the surface of flexible strand 31 though it may be impregnated in or incorporated in flexible strand 31 using any of the suitable methods described above. Flexible strand 31 can be employed in a variety of applications but is particularly suitable for use as a suture or for the fabrication of a mesh or fabric material, which may be employed as a radioactive source. Flexible strand 31 has the advantage that it can be cut to the desired size and that it can be employed in a variety of different configurations such as a wrap around a delivery device, woven through a stent or porous implant or sewn or tied to a part of the body to be treated. Flexible strand 31 may have a variety of different flexibilities. Preferably, flexible strand 31 is sufficiently flexible that it will bend under its own weight such that flexible strand 31 will behave like a piece of string or a suture or the like. Various other applications for the flexible strand 31 will be apparent to those of skill in the art.

Figure 6A:
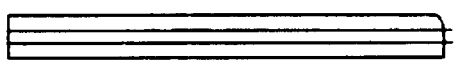
FIG. 6A shows a cross-sectional view of a fabric material with a radioactive material on a surface of the fabric material.
Figure 6B:
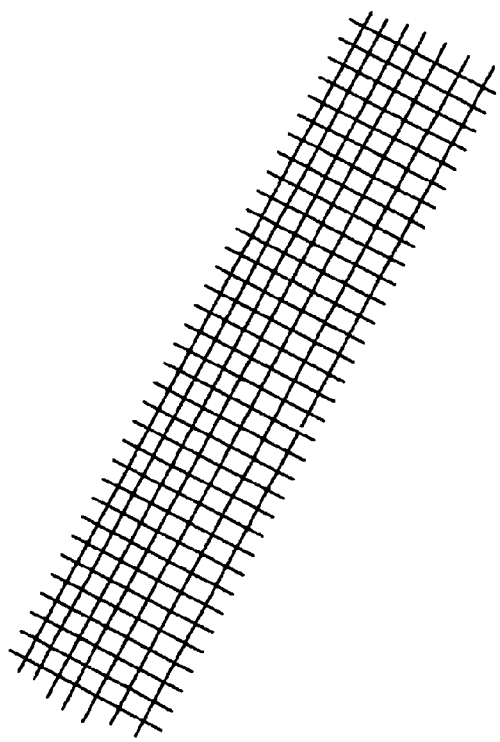
FIG. 6B shows a perspective view of a mesh made from the fabric material of FIG. 6A.

FIGS. 6A–6B show a fabric material 40 with a radioactive material 41 on the surface of the fabric 40. This fabric material 40 can be employed in the same manner as the film 10 shown in FIG. 1 or it can be used in a variety of other applications. The fabric material 40 has the advantage that it is porous and thus will allow passage of fluids therethrough. As a result, this type of radiation delivery device breathes which may be an advantage in helping to prevent infection. Moreover, the fabric material 40 can be attached to the body or other devices in any number of ways some of which may take advantage of the weave of the fabric in order to provide a secure attachment. The fabric material 40 may be tightly woven or loosely woven to form a mesh material, depending on the particular application for which it is to be used. The fabric material may optionally be coated with an outer coating 42 on the outside of the radioactive material 41 to isolate the radioactive material 41 from contact with the body, if desirable. The fabric material is preferably sufficiently flexible that it will deform under its own weight so that it can easily conform to the desired shape.

Figure 7A:
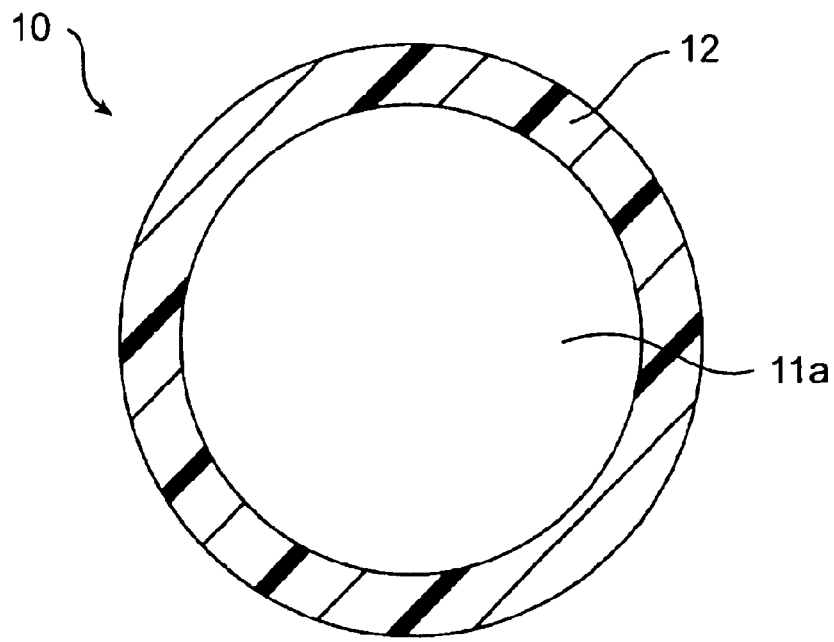
FIGS. 7A–7B illustrate cross-sectional views of a microsphere radiation delivery device according to one embodiment of the present invention.
Figure 7B:
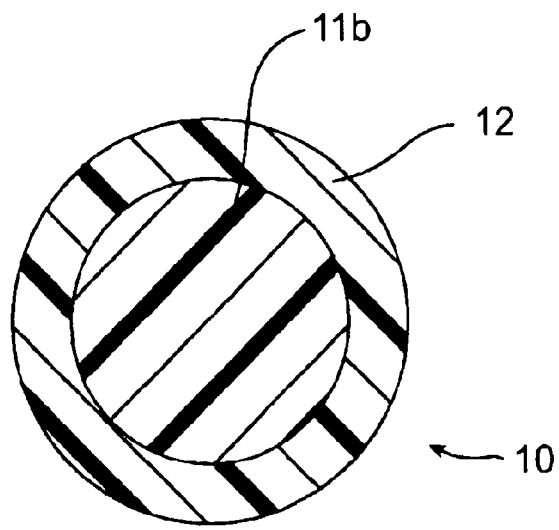

With reference to FIGS. 7A–7B, radiation delivery devices 10 formed from individual microspheres are illustrated in cross-section. In FIG. 7A, a hollow microsphere substrate 11a coated with a layer of radiation source material 12 is depicted. FIG. 7B illustrates a solid microsphere substrate 11b coated with radiation source material 12. Pellets may also be made which are similar to the microspheres shown in FIGS. 7A–7B.

Figure 8:
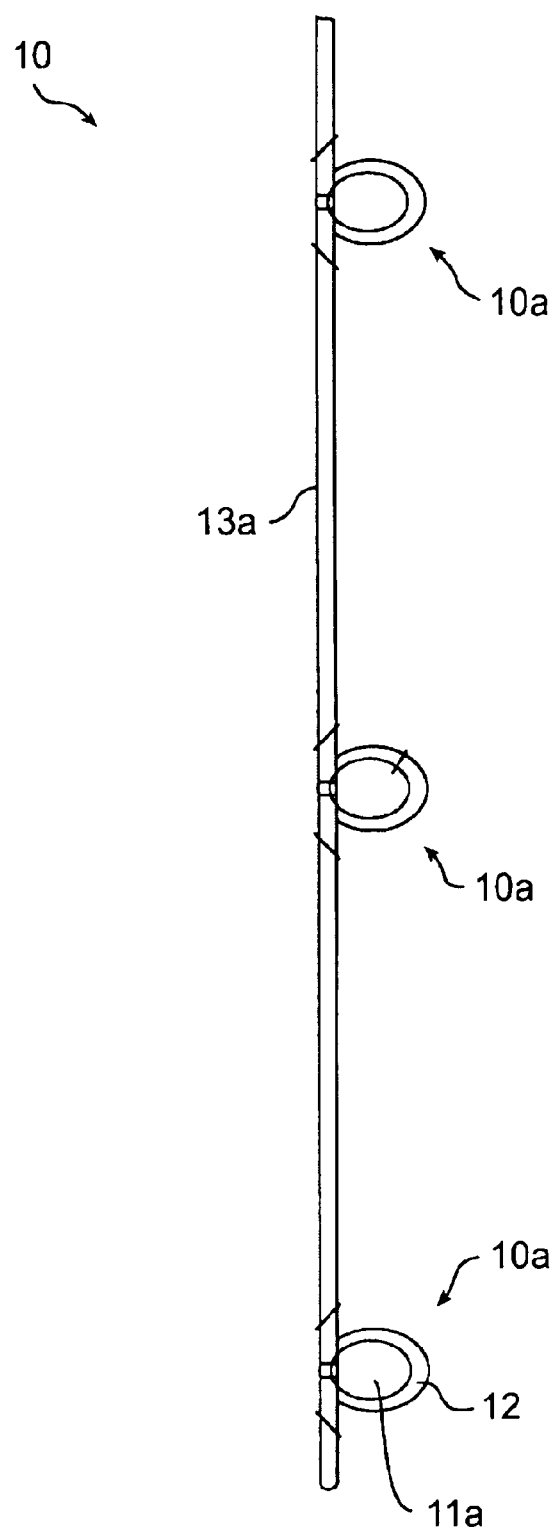
FIG. 8 illustrates a radiation delivery device comprising a fiber with multiple microspheres containing radioactive material attached thereto.

FIG. 8 shows a radiation delivery device 10 comprising a fiber structure 13a with microspheres 10a attached thereto. The microspheres 10a may be formed from a hollow microsphere substrate 11a coated with a radiation source material 12 as shown in FIG. 7A or with a solid microsphere substrate 11b as shown in FIG. 7B. The fiber structure 13a can be employed in a manner similar to the film of FIG. 1 or the mesh shown in FIG. 6 above.

Preferably the radiation source material is located on the outer surface of the delivery device. Locating the radiation source material on the outer surface of the device minimizes the extent of self-shielding and thereby reduces the amount of radiation source material required to achieve a desired therapeutic activity. It is believed that such a preferred configuration is made possible due to the unique proprieties of Pd-103 and the novel methods for incorporating the radiation source material into the delivery devices described herein. More particularly, the methods for incorporating the radiation source material into the delivery devices described herein are believed to result in sufficient bonding strength of the Pd-103 to the substrate to adequately prevent the migration of the radiation source material away from the delivery device during the time period that the Pd-103 emits potentially harmful levels of radiation. Moreover, it is considered that Pd-103 is sufficiently biocompatible that it can be employed in direct contact with at least some body tissue without producing significant detrimental effects.

However, if desired for an enhanced degree of safety or for specific applications, particularly in sensitive areas of the body, the delivery device can optionally be coated or sealed by an inert biocompatible material to inhibit migration or diffusion of the radiation source material into the patient. Such biocompatible materials can include films or coatings of polymers such as polyolefins, acrylates, polyurethanes, polyamides, polyimides, polyesters, polyvinyl chloride, cellulose esters, polysulfones, cyanoacrylates, modified versions of any of these materials and mixtures thereof. Alternatively, the biocompatible materials can be biocompatible metals such as titanium, stainless steel, tantalum, platinum, palladium or gold. Such biocompatible materials can be applied to the substrate containing radioactive material using any method known in the art. Of course, the self-shielding properties of such materials should be taken into consideration and minimized or at least equalized over the entire substrate, where possible.

The amount of radiation source material incorporated into the delivery device depends primarily upon the therapeutic radiation dosage required and the activity of the particular radioactive Pd-103, which is employed. For instance, a specific activity of at least 2.5 Ci/g is usually desirable for therapeutic brachytherapy applications. The total radiation level emitted by the delivery device, i.e., the therapeutic activity, is more accurately expressed as an apparent value in mCi measured just outside the radiation delivery device which takes into account any self-shielding within the device which may occur, however minimal. By adjusting the specific activity of the radiation source material and the amount of the radiation source material incorporated into the delivery device, the therapeutic activity level of the delivery device can be adjusted to preferred apparent activity levels of from about 0.5 $\mu$Ci to about 300 Ci per device and more preferably from about 0.5 mCi to about 30 Ci per device is employed.

Directional Devices

In another embodiment of the present invention, the radiation delivery devices can be fabricated to provide a directional radiation distribution. More specifically, if a particular treatment demands that radiation need only be directed towards a particular location, it may be advantageous to fabricate a directional radiation delivery device which can be employed to selectively irradiate neighboring tissue without irradiating other neighboring tissue.

Directional devices can be made in at least two ways, selectively shielding a part of the device or controlling the location of the radiation source material relative to the substrate. In the first alternative, the device may be selectively shielded at predetermined locations to provide for non-uniform, i.e., directional, radiation distribution. Such selective shielding can be accomplished by the incorporation of a shielding component into the delivery device at one or more predetermined locations or by fabricating all or a portion of the substrate from a shielding material. Shielding components can include radiation absorbing materials such as tin, silver, platinum, gold, tungsten, stainless steel, lead, brass, copper, or alloys thereof. More preferably, biocompatible shielding components are employed. The various embodiments of the flexible or deformable radiation delivery devices described herein can be directly adhered or attached to a shielding substrate in any suitable manner in order to provide a directional device.

Alternatively, directional radiation distributions can be accomplished by controlling the location of the radiation source material in or on the substrate and/or the location of the substrate in the overall delivery device. For example, the radiation source material may be applied to only one side of a substrate. This can be effectuated by providing some type of shielding material as the substrate, incorporating a shielding material into the substrate or even by provide a relatively large substrate such that radiation from the radiation source material has to travel a larger distance in one direction than another direction to impact body tissue. Since the effect of the radiation from palladium-103 is inversely proportional to the distance traveled by the radiation, a significant decrease in the exposure level of adjacent body tissue can be achieved merely by requiring the radiation to traverse such a distance or vary the attenuation on the surface of the device by providing a variation in the relative amounts of shielding. Alternatively, the depth at which the radioactive material is located within the substrate can be varied in order to vary the attenuation of the radiation and thereby give the desired directional effect to the device.

Optionally, the radiation delivery devices of the present invention can further include a marker to enhance imaging of the delivery devices once inside the body. The marker is generally comprised of a high atomic number element which, as a result of its high atomic number, is X-ray opaque. Suitable examples of such elements are known to persons skilled in the art and include lead, barium, gold, tungsten, cobalt, platinum and rhodium. The marker can also be fabricated in a way that the orientation of the device, if significant, can be determined from the orientation of the marker in an x-ray, i.e. by providing a non-symmetrical marker having a known orientation relative to the radiation delivery device. This type of marker is particularly useful for the directional radiation delivery devices of the present invention.

The following examples are included to further illustrate the invention.

EXAMPLE 1

A target for use in the charged particle accelerator is prepared by depositing rhodium metal onto a suitable substrate such as a copper or a silver substrate. The rhodium target thus prepared is then placed in a charged particle accelerator such as a cyclotron and bombarded with protons or deuterons. The energy of the impacting particles is chosen so substantially the only radioactive material created on the rhodium target is Pd-103, that is, the Pd-103 is carrier-free The rhodium metal containing the carrier-free Pd-103 is then placed in a hot cell wherein the rhodium metal is removed from the substrate by, for example, etching away with $HNO_3$. This removal is preferably accomplished by mechanically disrupting the continuity of the rhodium layer on the substrate as by perforating the surface with a sharply pointed impact tool. The exposed substrate surface is covered to protect it and the perforated target is immersed in a $HNO_3$ bath. A solution containing rhodium flakes results, which is filtered to recover the solid rhodium flakes containing Pd-103. The recovered rhodium flakes are rinsed on the filter and the flakes together with the filter are placed in a crucible and heated to decompose the filter leaving the rhodium metal flakes containing the Pd-103.

The rhodium metal flakes thus obtained are then partially dissolved in molten $NaHSO_4$ and the resulting $NaHSO_4$/rhodium flake mixture is dissolved in dilute HCl which provides soluble rhodium salts dissolved in dilute HCl. This procedure is normally repeated several times so as to dissolve any remaining rhodium metal containing carrier-free Pd-103.

EXAMPLE 2

This procedure demonstrates a procedure for the electroless plating of carrier-free Pd-103 onto a graphite substrate.

Initially, the graphite substrate was cleaned by ultra-sound or sonication using deionized water.

Once cleaned, the graphite substrate was pretreated with $SnCl_2$. The stannous ions produced in this step attract palladium ions later in the activation process.

The pretreated graphite substrate was then activated with a $PdCl_2$/HCl solution. The stannous ions from the previous step cause the $Pd^{2+}$ ions from $PdCl_2$ to reduce to $Pd^0$ and to adhere to the substrate. These $Pd^0$ sites form a catalytic surface on the pellets which enhances the deposition of radioactive Pd-103 onto the substrate in the subsequent plating step.

Carrier-free Pd-103 was then deposited on the activated graphite substrate by submerging the substrate in a heated solution of carrier-free Pd-103. Once the deposition reaction subsided, the graphite substrate plated with carrier-free Pd-103 was then dried and cooled to provide a radiation delivery device in accordance with the present invention.

EXAMPLE 3

The procedure of Example 2 was followed except that a polyurethane material was employed as the substrate to provide a flexible substrate. A flexible radiation delivery device was obtained.

EXAMPLE 4

A flexible film including a radioactive material was fabricated in accordance with the process of Example 3. The film was then adhered to a gold shield thin enough to be flexible. The gold shield provided significant attenuation of the radiation and as a result a flexible, directional radiation device was obtained.

The foregoing examples have been provided for the purpose of illustration and description only and are not to be considered as limiting the scope of the invention in any way. The scope of the invention is to be determined from the claims appended hereto.

What is claimed is:

1. A radiation delivery device, which comprises:
   a substantially non-conductive, flexible substrate selected from the group consisting of flexible fiber and flexible film formed from a radiation compatible material and which is sufficiently flexible to deform under its own weight, and
   a sufficient amount of radioactive palladium-103 bonded to the outer surface of the substrate to provide an apparent activity of the radiation delivery device, as measured adjacent to the surface of the substrate, of from about 0.5 $\mu$Ci to about 300 Ci/device, and wherein the radioactive palladium-103 comprises palladium-103 fabricated in a particle accelerator and said palladium-103 forms at least a substantial portion of the outer surface of the radiation delivery device such that the radioactive palladium-103 can be positioned closely adjacent to, or in direct contact with, a location to be treated with radiation.

2. A radiation delivery device as claimed in claim 1, wherein the radioactive palladium-103 is substantially homogeneously dispersed over the entire outer surface of the substrate to thereby provide a substantially uniform distribution of radiation from the radiation delivery device.

3. A radiation delivery device as claimed in claim 1, wherein the radioactive palladium-103 is non-uniformly dispersed over the outer surface or within the outer surface of the substrate to thereby provide a directional distribution of radiation from the radiation delivery device.

4. A radiation delivery device as claimed in claim 1, wherein the substrate comprises at least one material selected from the group consisting of: polymeric materials, ceramic materials, hydrogels, metals, graphite and ion exchange resins.

5. A radiation delivery device as claimed in claim 1, wherein the substrate comprises a flexible material selected from the group consisting of elastomers, gels and foams.

6. A radiation delivery device as claimed in claim 1, further comprising a protective coating layer located on the outside of the radioactive layer.

7. A radiation delivery device as claimed in claim 1, having an apparent activity of from about 0.5 mCi to about 30 Ci per device.

8. A radiation delivery device as claimed in claim 1, wherein the substrate comprises at least one polymeric material selected from the group consisting of polyethylene glycol and polyethylene glycol-polyethylene oxide copolymers, polyurethanes and silicones.

9. A radiation delivery device as claimed in claim 1, further comprising a radiation shielding layer located on a side of the substrate opposite a side of the substrate on which the carrier-free palladium-103 is bonded.

10. A radiation delivery device as claimed in claim 1, wherein the palladium-103 is bonded to the substrate by electroless plating.

11. A deformable radiation delivery device which comprises:

a deformable substrate, and a sufficient amount of radioactive palladium-103 bonded to the substrate to provide an apparent activity of the radiation delivery device, as measured adjacent to the surface of the substrate, of from about 0.5 $\mu$Ci to about 300 Ci/device, and wherein the radioactive palladium-103 comprises palladium-103 fabricated in a particle accelerator and said palladium-103 is bonded to the deformable substrate in a manner whereby substantially no radioactive palladium-103 detaches from the deformable substrate under normal use conditions, wherein the radioactive palladium-103 is bonded directly to the outer surface of the substrate by electroless plating.

12. A deformable radiation delivery device as claimed in claim 11, wherein the deformable substrate comprises an elastomer, gel or foam.

13. A deformable radiation delivery device as claimed in claim 11, further comprising a deformable coating of a biocompatible material on the outer surface of the radiation delivery device.

14. A radiation delivery device claimed in claim 11, wherein the substrate comprises at least one polymeric material selected from the group consisting of polyethylene glycol and polyethylene glycol-polyethylene oxide copolymers, polyurethanes and silicones.

15. A radiation delivery device as claimed in claim 11, further comprising a radiation shielding layer located on a side of the substrate opposite a side of the substrate on which the carrier-free palladium-103 is bonded.

16. A radiation delivery device as claimed in claim 11, wherein the substrate comprises at least one flexible polymeric material.

17. A radiation delivery device as claimed in claim 11, wherein the radioactive palladium-103 is substantially homogeneously dispersed over the entire outer surface of the substrate to thereby provide a substantially uniform distribution of radiation from the radiation delivery device.

18. A radiation delivery device as claimed in claim 11, wherein the radioactive palladium-103 is non-uniformly dispersed over the outer surface or within the outer surface of the substrate to thereby provide a directional distribution of radiation from the radiation delivery device.

19. A radiation delivery device as claimed in claim 11, wherein the substrate is substantially non-conductive.

* * * * *